United States Patent [19]

D'Amico

[11] 4,171,213

[45] Oct. 16, 1979

[54] N-SUBSTITUTED OXYBENZOTHIAZOLINE DERIVATIVES AND THEIR USE AS PLANT GROWTH REGULANTS

[75] Inventor: John J. D'Amico, Olivette, Mo.

[73] Assignee: Monsanto Company, St. Louis, Mo.

[21] Appl. No.: 907,390

[22] Filed: May 18, 1978

[51] Int. Cl.$^2$ ..................... C07D 277/62; A01N 9/12
[52] U.S. Cl. ..................................... 71/90; 548/170; 548/157
[58] Field of Search ................................. 260/304 B

[56] References Cited

U.S. PATENT DOCUMENTS

| 3,993,468 | 11/1976 | D'Amico | 71/90 |
| 4,075,216 | 2/1978 | D'Amico | 71/90 |

Primary Examiner—Nicholas S. Rizzo
Attorney, Agent, or Firm—Patricia A. Coburn; Donald W. Peterson

[57] ABSTRACT

The present invention relates to compounds of the formula

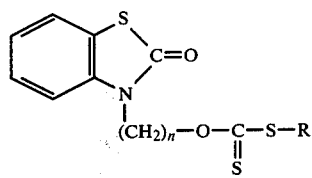

wherein R represents

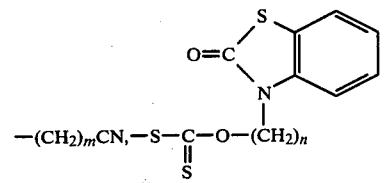

$-(CH_2)_mCN, -S-C-O-(CH_2)_n$
$\phantom{-(CH_2)_mCN, -S-}\|$
$\phantom{-(CH_2)_mCN, -S-}S$ and potassium and sodium cathions; n is an integer of from 1 to 2; and m is an integer of from 1 to 2. The invention relates to the use of said compounds in a method of regulating leguminous plant growth as well as to plant growth regulant compositions.

12 Claims, No Drawings

N-SUBSTITUTED OXYBENZOTHIAZOLINE DERIVATIVES AND THEIR USE AS PLANT GROWTH REGULANTS

SUMMARY OF THE INVENTION

This invention is concerned with novel N-substituted 2-oxo-3-benzothiazoline derivatives. It also relates to the use of these compounds in regulating the growth of leguminous plants. The invention further relates to the use of the novel 2-oxo-3-benzothiazoline derivatives in plant growth regulant compositions.

DETAILED DESCRIPTION OF THE INVENTION

The compounds employed in the present invention are 2-oxo-3-benzothiazoline derivatives of the formula

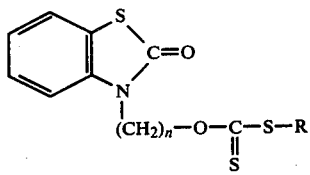

wherein R is selected from the group consisting of

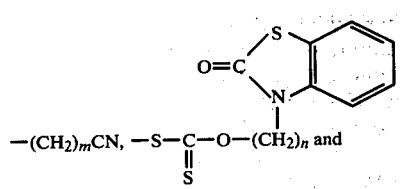

$-(CH_2)_m CN$, $-S-C(=S)-O-(CH_2)_n$ and potassium and sodium cations; n is an integer of from 1 to 2; and m is an integer of from 1 to 2.

When R is potassium or sodium cation, a salt is formed; the preferred salt is the one formed when potassium is the cation.

Compunds of the invention wherein R is potassium or sodium cation can be formed by mixing 3-(hydroxymethyl)-2-benzothiazolinone or 3-(2-hydroxy-ethyl)-2-benzothiazolinone with carbon disulfide and a hydroxide, such as KOH or NaOH, and allowing the resulting mixture to react. When potassium hydroxide is used the reaction can be illustrated as follows:

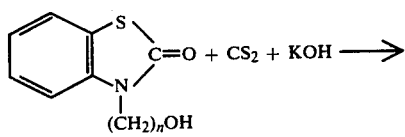

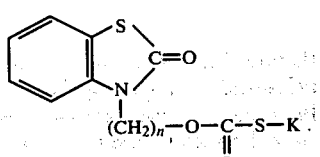

Example 1 illustrates the above process in greater detail.

EXAMPLE 1

To a stirred charge containing 0.25 mol of 3-(2-hydroxyethyl)-2-benzothiazolinone in 500 ml of carbon disuflide, 16.5 g (0.25 mol) of potassium hydroxide was added in small portions at 20°-25° C. over a 10 minute period. After stirring at 25°-30° C. for 24 hours, 600 ml of ethyl ether was added, and stirring continued for 15 minutes. The product xanthic acid, O-[2-(2-oxo-3-benzothiazolinyl)-ethyl]ester, S-potassium salt, was collected by filtration and air-dried at 25°-30° C. The data is summarized below:

| Compound | % | % N | |
|---|---|---|---|
| No. 1 | Yield | Calc'd | Found |
| 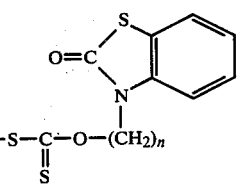 | 99 | 4.52 | 4.47 |

S-potassium O-[2-(2-oxobenzothiazoline-3-yl) ethyl]-xanthic acid and S-potassium O-[(2-oxobenzothiazolin-3-yl)-methyl] xanthic acid can be used to prepare compounds of the invention wherein R is $-(CH_2)_m CN$ and

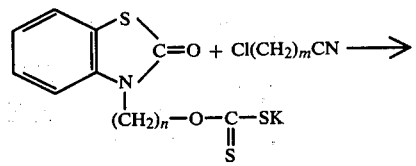

and where m and n have the values previously assigned, according to the following general reactions:

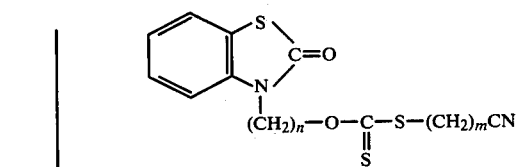

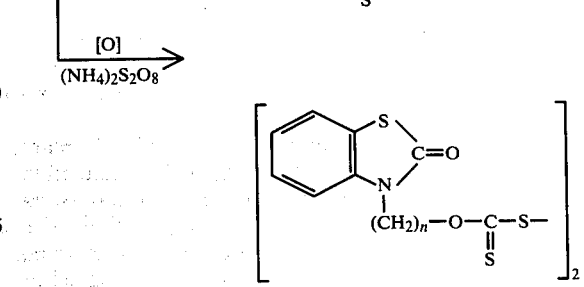

According to the above reactions, compounds of the invention were prepared as illustrated in Examples 2 and 3.

EXAMPLE 2

To a stirred slurry containing 31 g (0.1 mol) of S-potassium O-[2-(2-oxo-3-benzothiazolinyl)ethyl] xanthic acid in 400 ml of water 8.5 g (0.11 mol) of chloroacetonitrile was added in one portion. The reaction mixture was stirred at 25°-30° C. for two days. After the addition of 600 ml of ethyl ether, stirring was continued for 30 minutes. The impurities were removed by filtration. The separated ether layer of the filtrate was washed with water until neutral to litmus and dried over sodium sulfate. The ether was removed in vacuo at maximum temperature of 80°-90° C. at 1-2 mm. Carbonodithioic Acid, S-(Cyanomethyl)ester, O-[2-(2-oxo-3-benzothiazolinyl)ethyl] ester, a dark amber viscous liquid, was obtained in 35% yield.

| Compound No. 2 | % Yield | % N Calc'd | % N Found | % S Calc'd | % S Found |
|---|---|---|---|---|---|
| 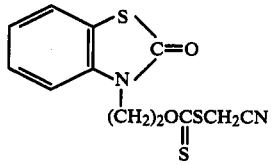 | 35 | 9.02 | 9.90 | 30.99 | 30.12 |

EXAMPLE 3

To a stirred solution containing 31 g (0.1 mol) of S-potassium O-[2-(2-oxo-3-benzothiazolinyl)ethyl] xanthic acid in 500 ml of water, a solution containing 12.6 g (0.055 mol) of ammonium persulfate in 100 ml of water was added dropwise at 0°-10° C. over a 20 minute period. After stirring at 0°-10° C. for 1.5 hours, the solid was collected by filtration, washed with water until neutral and air-dried at 25°-30° C., Formic acid, thiono-, bis-, 1,1'-dithio-, bis[2-(2-oxo-3-benzothiazolinyl)ethyl] ester, mp 151°-4° C. with decomposition, was obtained in 67% yield. After recrystallization from DMF, Compound 3 melted at 158°-160° C. with decomposition.

| Compound No. 3 | % Yield | % N Calc'd | % N Found | % S Calc'd | % S Found |
|---|---|---|---|---|---|
| 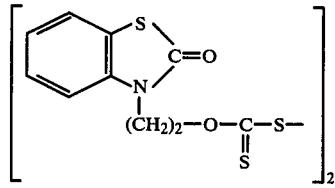 | 67 | 5.18 | 5.24 | 35.58 | 35.44 |

As noted above, the compounds of the present invention have been found to be effective in the regulation of leguminous plant growth; the preferred legume is soybean (Glycine max).

The terms "plant growth regulant effect", "plant growth regulation" or words to that effect, are used in this specification and in the claims to mean the causation by the chemicals of the present invention, of a variety of plant responses which achieve a promotion, inhibition or modification of any plant physiological or morphological process. It should additionally be recognized that various plant responses may also result from a combination or sequence of both physiological and morphological factors. Such plant responses are most readily observed as changes in size, shape, color or texture of the treated plant or any of its parts. The above changes may be characterized as an acceleration or retardation of plant growth, stature reduction, leaf or canopy alternation, increased branching, increased fruit set, accelerated fruit set and the like. While many of these modifications are desirable in and of themselves, most often it is their effect on the economic result that is of most importance. For example, a reduction in stature of the plant permits the growing of more plants per unit area.

It is to be understood that the regulation of desirable leguminous crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention, it has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In accordance with the practice of the invention, several plant growth regulating compositions were formulated by mixing various N-substituted 2-oxo-3-benzothiazoline compounds as the active ingredient, with acetone containing TWEEN 20 surfactant. The compositions thus formulated exhibited plant regulatory properties as illustrated by the test set forth in Example 4.

EXAMPLE 4

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition of active ingredient, acetone and TWEEN 20 surfactant was applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and two weeks after application represent the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction, or an increase in growth in excess of 25% of that of the control plants, i.e., growth stimulation.

Table III below summarizes the results and observations made in accordance with Example 4 when the N-substituted 2-oxo-3-benzothiazolines of the invention were utilized as the active ingredient at several rates. Some slight phytotoxicity was noted, especially at the higher application rates.

Table III

| Compounds of Example | RATE Lbs/Acre (Kilos/hectare) | Response |
| --- | --- | --- |
| 1 | 6.0 (6.72) | Stature reduction, leaf distortion, thick leaf texture, inhibition of apical development, slight leaf burn. |
|  | 6.0 (6.72) | Leaf distortion, altered canopy, thick leaf texture. |
|  | 3.0 (3.36) | Leaf distortion. |
|  | 1.2 (1.34) | No response noted. |
| 3 | 6.0 (6.72) | Stature reduction, axillary bud development, leaf distortion, thick leaf texture, inhibition of apical development, slight leaf burn. |
|  | 3.0 (3.36) | Leaf distortion, inhibition of apical development, slight leaf burn. |

Further plant growth regulating activity was demonstrated when the novel N-substituted 2-oxo-3-benzothiazolines of the present invention were tested according to the procedure described in Example 5.

EXAMPLE 5

A number of soybean plants, variety Williams, are grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 is used as a surfactant.

When the fifth trifoliate leaf (four to five weeks) was fully expanded, the treated plants were compared with the non-treated control plants and the observations recorded.

Table V below summarizes the results and observations made in accordance with the above procedure.

TABLE IV

| Compounds of Example | RATE Lbs/Acre (Kilos/hectare) | Response |
| --- | --- | --- |
| 1 | 2.5 (2.80) | Stature reduction, stem distortion, leaf alteration, altered canopy, decreased dry matter accumulation. |
|  | 0.5 (0.56) | Decreased dry matter accumulation. |
|  | 0.1 (0.11) | Decreased dry matter accumulation. |
| 2 | *2.5 (2.80) | Leaf distortion, altered canopy, leaf alteration, leaf inhibition, slight leaf burn, decreased dry matter accumulation. |
|  | *0.5 (0.58) | Leaf alteration, decreased dry matter accumulation. |
|  | *0.1 (0.11) | Decreased dry matter accumulation. |
| 3 | 2.5 (2.80) | Leaf alteration, slight leaf burn, decreased dry matter accumulation. |
|  | 0.5 (0.56) | Leaf alteration, decreased dry matter accumulation. |
|  | 0.1 (0.11) | Decreased dry matter accumulation. |

*Data combined from two tests.

Compound 1 was further tested according to the procedure described in Example 6.

EXAMPLE 6

Individual soybean plants, variety Corsoy, are grown from seed in 6-inch pots containing a good grade of top soil. Two pots of 4 week old plants (3–4 trifoliate stage) and two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15 percent in the average total height of the treated plants, when compared to the average total height of the control plants, demonstrates that the chemical is an effective plant growth regulator. These observations are repeated at four weeks after chemical application as a further evaluation of plant regulatory activity. The observations made on 4-week and 6-weekold plants, at 2 and 4 weeks form a composite evaluation.

Observations made utilizing the test procedure of Example 6 are summarized in Table V.

TABLE V

| Compound of Example | RATE Lbs/Acre (Kilos/hectare) | observations |
|---|---|---|
| 1 | 1.0 (1.12) | Enhanced pod set. |
| | 2.5 (2.80) | Early pod set, enhanced pod set, leaf distortion. |
| | 5.0 (5.60) | Early pod set, enhanced pod set, leaf distortion, leaf inhibition, axillary bud inhibition. |

In selecting the appropriate time and rate of application of the active ingredient, it will be recognized that precise rates will also be dependent upon the desired response, mode of application, plant variety, soil conditions and various other factors known to those skilled in the art. While a rate of up to 11.2 kilos per hectare may be used, rates below 6.72 kilos per hectare are preferred. In addition, it will be recognized that single or multiple applications may be used to exert the desired response.

In the practice of the invention, the active ingredient can be used alone or in combination with materials referred to in the art as adjuvants, in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid or organic origin, water, a wetting agent, dispersing agent or emulsifying agent or any suitable combination of these.

Illustrative finely-divided solid carries and extenders which are useful in plant growth regulating compositions of this invention include the talcs, clays, pumice, silica, diatomaceous earth, quartz, Fullers, earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the uniform distribution of the active ingredient. The application of liquid and particulate solid compositions of the active ingredient can be carried out by conventional techniques utilizing, for example, spreaders, power dusters, boom and band sprayers and spray dusters. The composition can also be applied from airplanes as a dust or spray.

Compositions of this invention generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed:

1. A compound of the formula

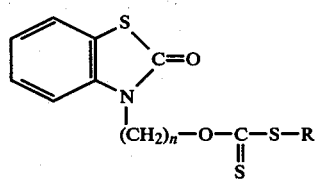

wherein R is selected from the group consisting of $-(CH_2)_m CN$,

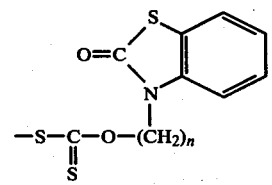

and potassium and sodium cations;

n is an integer of from 1 to 2; and m is an integer of from 1 to 2.

2. A compound according to claim 1 which is

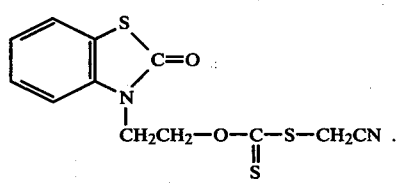

3. A compound according to claim 1 which is

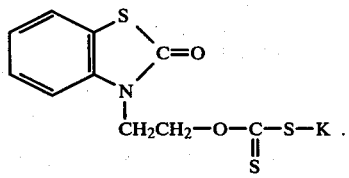

4. A compound according to claim 1 which is

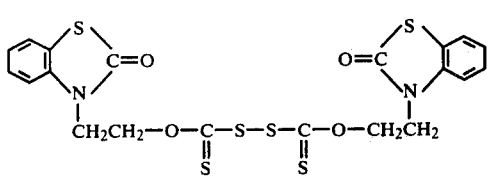

5. A method of influencing the growth of leguminous plants which method comprises applying to said leguminous plants or their habitat an effective plant growth regulating amount of a compound of the formula

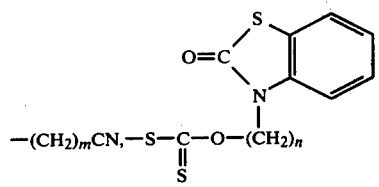

wherein R is selected from the group consisting of —$(CH_2)_mCN$,

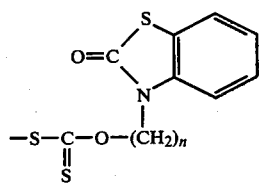

and potassium and sodium cations; n is an integer of from 1 to 2; and m is an integer of from 1 to 2.

6. A method according to claim 5 wherein the compound is

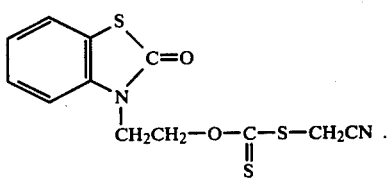

7. A method according to claim 5 wherein the compound is

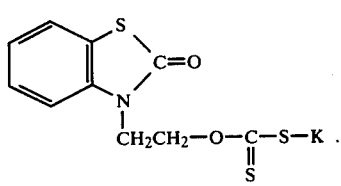

8. A method according to claim 5 wherein the compound is

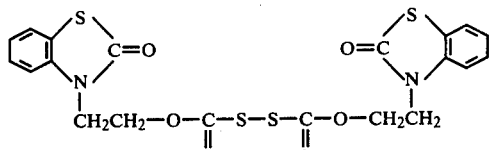

9. A plant growth regulating composition comprising inert adjuvant and as the active ingredient, from about 5 to about 95 parts by weight of a compound of the formula

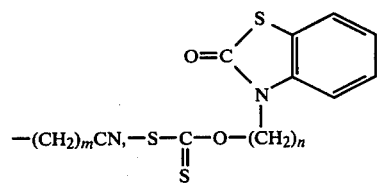

wherein R is selected from the group consisting of —$(CH_2)_mCN$,

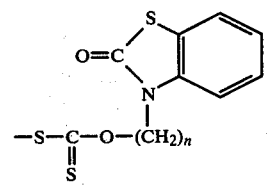

and potassium and sodium cations;
n is an integer of from 1 to 2; and m is an integer of from 1 to 2.

10. A composition according to claim 9 wherein the active ingredient is

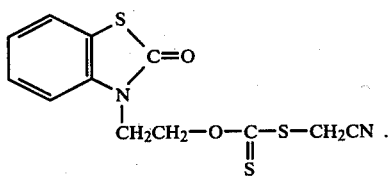

11. A composition according to claim 10 wherein the active ingredient is

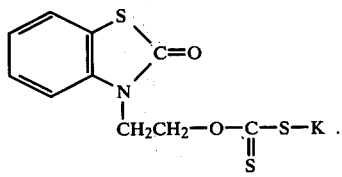

12. A composition according to claim 10 wherein the active ingredient is

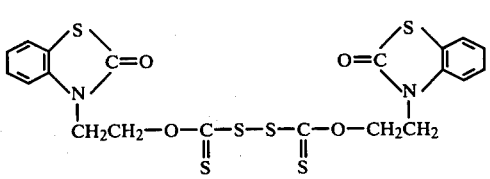

* * * * *

UNITED STATES PATENT AND TRADEMARK OFFICE
CERTIFICATE OF CORRECTION

PATENT NO. : 4,171,213
DATED : October 16, 1979
INVENTOR(S) : John J. D'Amico

It is certified that error appears in the above-identified patent and that said Letters Patent are hereby corrected as shown below:

Col. 9, lines 16-25, Claim 5, the first formula, and
Col. 10, lines 13-22, Claim 9, the first formula

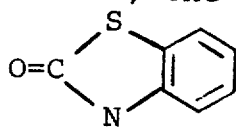

" 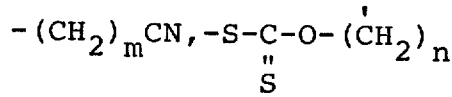 "

should read as follows:

-- 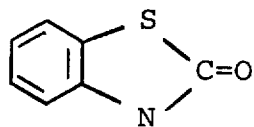

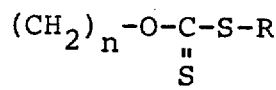 --

Signed and Sealed this

Twenty-sixth Day of February 1980

[SEAL]

Attest:

SIDNEY A. DIAMOND

Attesting Officer    Commissioner of Patents and Trademarks